US011175276B2

(12) United States Patent
Frankel et al.

(10) Patent No.: US 11,175,276 B2
(45) Date of Patent: Nov. 16, 2021

(54) FABRIC TESTING HARDWARE

(71) Applicant: Gerber Technology LLC, Tolland, CT (US)

(72) Inventors: Scott M Frankel, Berkeley, CA (US);
James F O'Brien, El Cerrito, CA (US);
Nathan Mitchell, Richmond, CA (US);
David T Jackson, Redwood City, CA (US)

(73) Assignee: GERBER TECHNOLOGY LLC, Tolland, CT (US)

( * ) Notice: Subject to any disclaimer, the term of this patent is extended or adjusted under 35 U.S.C. 154(b) by 150 days.

(21) Appl. No.: 16/714,425

(22) Filed: Dec. 13, 2019

(65) Prior Publication Data

US 2020/0191764 A1    Jun. 18, 2020

Related U.S. Application Data (60) Provisional application No. 62/779,421, filed on Dec. 13, 2018.

(51) Int. Cl.
    *G01N 33/36*    (2006.01)
    *G01N 3/06*     (2006.01)
    *G01N 3/08*     (2006.01)

(52) U.S. Cl.
     CPC ........... *G01N 33/367* (2013.01); *G01N 3/068* (2013.01); *G01N 3/08* (2013.01)

(58) Field of Classification Search
     CPC .. G05B 23/0294; G01N 33/367; G01N 3/068; G01N 3/08
     USPC ......................................................... 73/800
     See application file for complete search history.

(56) References Cited

U.S. PATENT DOCUMENTS

| 2,375,209 | A  | * | 5/1945  | Basquin | G01N 3/24 |
|-----------|----|----|---------|---------|-----------|
|           |    |    |         |         | 73/846    |
| 2,622,131 | A  | * | 12/1952 | McKee   | B60F 1/04 |
|           |    |    |         |         | 324/217   |
| 2018/0024015 | A1 | * | 1/2018 | Berme  | G01L 5/107 |
|           |    |    |         |         | 73/760    |

FOREIGN PATENT DOCUMENTS

| GB | 590639 A      | 7/1947 |
|----|---------------|--------|
| WO | 2007/026143 A1| 3/2007 |

OTHER PUBLICATIONS

International Search Report and Written Opinion of the International Searching Authority issued in corresponding international application No. PCT/US2019/066371, dated Apr. 29, 2020. (9 pages).

(Continued)

*Primary Examiner* — Octavia Hollington
(74) *Attorney, Agent, or Firm* — Day Pitney LLP; Valeriya Svystun (57) ABSTRACT

A material testing apparatus comprising a frame having three or more tracks, and a plurality of mounts positioned within the three or more tracks. The mounts including an attachment mechanism to attach the mounts to a material being tested. The mounts including a force measurement elements. Some of the mounts free mounts that move in a track slot within the track, the free mounts free to move to any position within the track slot. The apparatus further comprising a data collector to collect data from the force measurement elements in the mounts when the material is placed under stress, to characterize the material.

20 Claims, 7 Drawing Sheets

(56) References Cited

OTHER PUBLICATIONS

David Clyde, Joseph Teran, and Rasmus Tamstorf. 2017. Modeling and data-driven parameter estimation for woven fabrics. In Proceedings of the ACM SIGGRAPH / Eurographics Symposium on Computer Animation (SCA '17), Stephen N. Spencer (Ed.). ACM, New York, NY, USA, Article 17, 11 pages.

Eder Miguel, Derek Bradley, Bernhard Thomaszewski, Bernd Bickel, Wojciech Matusik, Steve Marschner, and Miguel A. Otaduy Data-Driven Estimation of Cloth Simulation Models. Comput. Graph. Forum 31, 2pt2 (May 2012), 519-528.

Eder Miguel, Rasmus Tamstorf, Derek Bradley, Sara C. Schvartzman, Bernhard Thomaszewski, Bernd Bickel, Wojciech Matusik, Steve Marschner, and Miguel A. Otaduy. Modeling and estimation of internal friction in cloth. ACM Trans. Graph. 32, 6, Article 212 (Nov. 2013), 10 pages.

Huamin Wang, Ravi Ramamoorthi, and James F. O'Brien. "Data-Driven Elastic Models for Cloth: Modeling and Measurement". ACM Transactions on Graphics, 30(4):71:1-11, Jul. 2011. Proceedings of ACM SIGGRAPH 2011, Vancouver, BC Canada.

Miguel et al, Data-Driven Estimation of Cloth Simulation Models, Eurographics 2012, vol. 31 (2012), No. 2, 10 pages, Oxford, UK and Malden, MA, USA.

Min-Hyung Choi, Steven C. Wilber, and Min Hong. Estimating material properties of deformable objects by considering global object behavior in video streams. Multimedia Tools Appl. 74, 10 (May 2015), 3361-3375.

Shan Yang and Ming Lin. 2015. Simultaneous estimation of elasticity for multiple deformable bodies. Comput. Animat. Virtual Worlds 26, (May 3-4, 2015), 197-206.

Wang et al, Data-Driven Elastic Models for Cloth: Modeling and Measurement, ACM Transaction on Graphics vol. 30, No. 4, ACM SIGGRAPH 2011, Vancouver, BC Canada. (11 pages).

\* cited by examiner

FIG. 6

FABRIC TESTING HARDWARE

RELATED APPLICATION

The present application claims priority to U.S. Patent Application No. 62/779,421 filed on Dec. 13, 2018, which is hereby incorporated by reference in its entirety.

FIELD

The present invention relates to material testing and in particular to providing a hardware system to enable determining of the mechanical properties of a planar material sample.

BACKGROUND

Fabric testing devices are used for measuring the mechanical properties of a fabric sample. These properties are characterized by a set of mechanical parameters that can be used in a fabric simulation so that the simulation will accurately reproduce the behavior of the sampled fabric. These parameters determine the relationship between the strain state at any point in the fabric and the resulting stress at that point.

Prior art fabric testing systems, such as the Kawabata Evaluation System (KES) provides one-dimensional stretch and shear testing separately but cannot provide testing for more complex strain configurations that may combine stretch in more than one direction or that combine stretch and shear. Furthermore, existing systems assume that the resulting stress will be correspond to the strain being tested, so that a stretch along one direction is assumed to produce only forces in the same direction. Real fabrics may generate stresses that are not aligned with the tested strain.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A material testing system is described that can provide multi-dimensional planar material testing. Instead of providing a one-dimensional measurement, which enables the tester to stretch the material in one of X, or Y, or XY shear, it can combine stretching in X, Y, and/or XY shear simultaneously. The device can also measure resulting elastic forces that may be in any combination of X, Y, or XY. For example, when stretching a sample along the X direction, there will typically be a resulting force along the X direction, but due to the Poisson effect there may also be resulting forces in the Y direction. In one embodiment, some of the materials tested may be anisotropic, so their behavior when stretched in one direction is different than their behavior when stretched in another direction. This means that devices that can only test in one direction would not provide complete data for such materials. Because the present testing system is capable of testing in all directions, it can explore the full strain space of the material, and therefore captures antisotropic behavior accurately. The present testing system enables characterizing stretch along any direction, not just X or Y.

This type of testing is important to provide data for fabric, or other material, modeling by computer simulation. In one embodiment, the system is also capable of recording the parameters of these tests. In one embodiment, the resulting data may be used for modeling fabric movement and display. Such material testing devices are used for measuring the mechanical properties of a fabric sample. These properties are characterized by a set of mechanical parameters that can be used in a fabric simulation so that the simulation will accurately reproduce the behavior of the sampled fabric.

The term fabric generally refers to cloth that typically is produced by weaving or knitting textile fibers. However, the material testing system may also be used for other planar materials, such as rubber, leather, paper, aluminum, or other sheet-like materials for which it would be useful to obtain mechanical properties. For simplicity, the description below refers to fabric, but one of skill in the art would understand that any deformable planar material may be similarly tested.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1A:
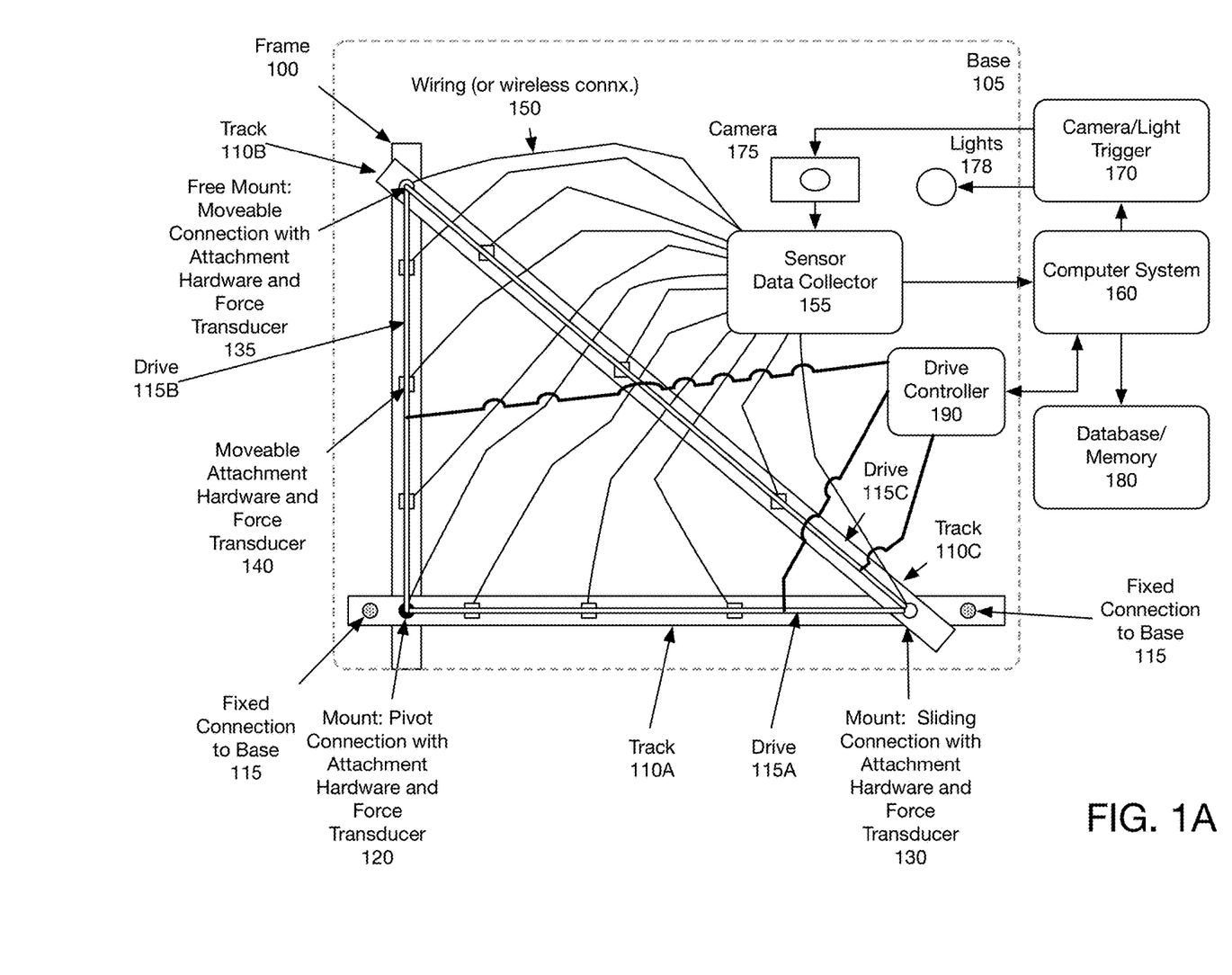
FIG. 1A an overview diagram of one embodiment of the material testing system.

FIG. 1A an overview diagram of one embodiment of the material testing system. The material testing system includes in one embodiment a frame including three tracks 110 which are used to attach the fabric for testing. While in one embodiment there are three tracks arranged in a triangle, in another embodiment, the tracks 110 may be arranged in a rectangular shape, or another shape. However, in one embodiment, the triangular shape is preferred because the triangular track can be configured to uniformly produce any desired strain without requiring that the movement of two or more tracks be mutually constrained.

The material testing system is designed to have a triangular sample of material affixed to a set of pins that are set into three tracks, with the three tracks arranged to form a triangle. The tracks are attached so that they can pivot and slide, as shown in the diagrams. The distances between the three pins that correspond to the vertices of the triangle are controlled by linear actuators. The distances between the pins directly determine the shape of the resulting triangle.

One track 110A, shown here on the bottom, is attached to a base 105 via fixed connections 115. In one embodiment, these fixed connections may be bolts. This is the "base" of the triangle which does not move. The second track 110B and third track 110C are coupled to the first track 110A, forming a triangle. The coupling is movable, so that the tracks can move with respect to each other.

Figure 3A:
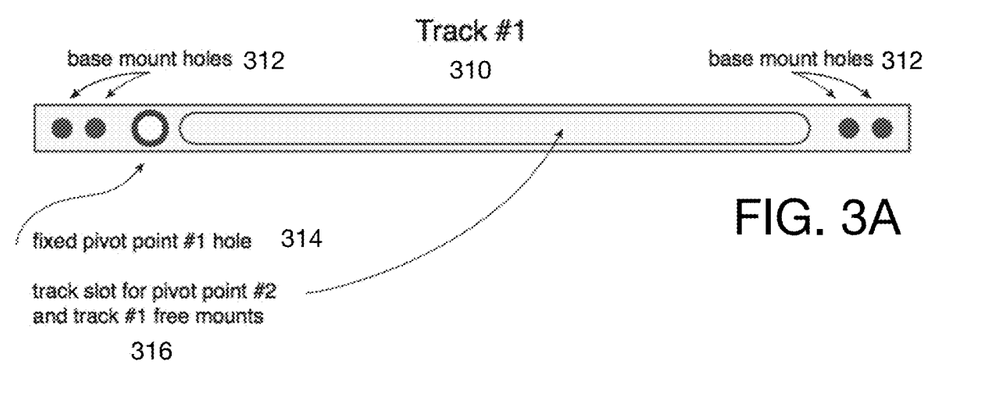
FIG. 3A-3C are illustrations of embodiments of each of the tracks for one embodiment of the system.
Figure 3B:
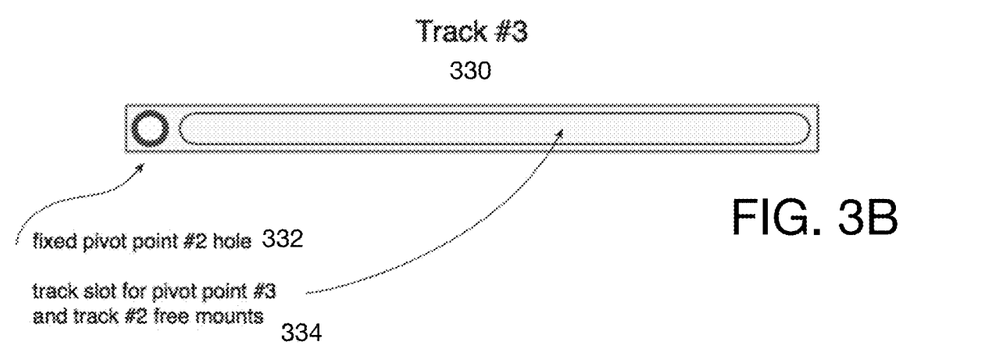
Figure 3C:
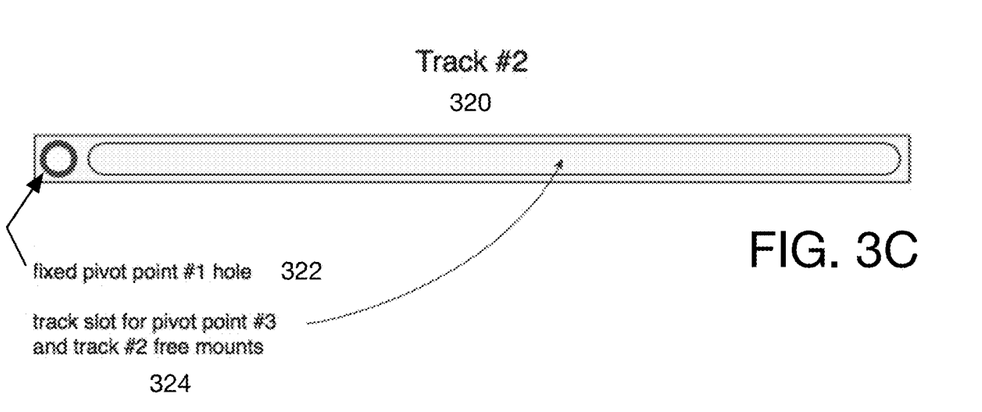

FIGS. 3A through 3C illustrate embodiments of the specific configurations of each of the tracks.

As shown in FIG. 3A Track 1 310 has two sets of base mount holes 312 which attach the track 310 to the base. This is the "base" of the triangle which does not move.

A second track 320, shown in FIG. 3C, is attached via a pivot connection 322 to the first track 310. The pivot connection 322 allows the track 320 rotate with respect to track 310. The pivot connection 322 includes attachment hardware, and in one embodiment is one of the points to which the fabric to be tested is coupled.

A third track 330, shown in FIG. 3B, is coupled to both the first track 310 and the second track 320. In one embodiment, the third track 330 also includes a fixed pivot point 332. The fixed pivot point is coupled to a track slot 316 in first track 310. This allows the third track 330 to move along the first track 310 and pivot. The track 320 and third track 330 both include a track slot, 324 and 334 respectively. The connection between track 2 320 and track 3 330 is via a moveable connection which can move along the slots of track 2 320 as well as track 3 330.

In one embodiment, if the frame is a rectangular shape, the system matches movement in parallel sides, to enable consistent testing of the entire fabric piece. Other shapes may also be utilized for the frame. Other shapes require that the track movements be balanced so that they enable consistent testing of the entire fabric piece.

Returning to FIG. 1A, within the track slots of each of track 110A, 110B, 110C there are movable attachment hardware elements 140, also referred to as free mounts 140, which can slide along the track and to which the fabric is attached. By making the attachment hardware elements 140 moveable, they move freely as the fabric is tested. In one embodiment, each of these hardware elements 140 include a force transducer to measure in real-time the force being placed on the fabric in that particular location. Because the free mounts 140 move freely along the track, the pins allow the fabric sample to stretch freely parallel to the tracks while remaining uniformly attached to the tracks. Without sliding pins, the cloth sample would not be in an approximately uniform state of strain.

In one embodiment, each track has three moveable free mounts 140. In another embodiment more or fewer free mounts 140 may be used. In one embodiment, the number of free mounts depends on the size of the frame. In one embodiment, the design may be set so that at its maximum extension there is a free mount approximately every 3 inches along the edge of the fabric, in addition to the track connection mounts. The appropriate spacing of free mounts depends on the size of the fabric sample and the rigidity of the sample. A sufficient number of free mounts should be used such that the sample does not pull away excessively between the attachments. Pull away refers to the material curving inward away from the track between the mounts. Pull away causes the strain in the sample to be nonuniform and interferes with accurate measurement. Excessive pull away would be mean that the interference with accurate strain measurement reaches a level where it compromises the accuracy required for a specific application. In the case of acquiring measurements for use in subsequent fabric simulation, in one embodiment the system is designed to have a pull away distance of less that 5% the width of the fabric sample being tested. In one embodiment, additional free mounts may be placed on the track to limit pull away.

In another embodiment, clips or similar attachments could be used to keep the edge of the material sample from moving away from the track while still allowing free movement parallel to the track.

In one embodiment, when the fabric is initially placed into the fabric testing apparatus the triangle is configured to form a square right triangle where the X edge and Y edge are set to the same initial length and where the X edge and Y edge are perpendicular to each other. Subsequently, linear actuators in the drives 115A, 115B, 115C are adjusted by drive controller 190 so that the X and Y edges may be longer or shorter than the initial setting and so that the X and Y edges may be of different lengths from each other. The diagonal edge may have its length adjusted so that the X and Y edges do not remain perpendicular to each other and may instead be set to form an arbitrary angle.

Given the initial lengths of the X and Y edges, the current lengths of the X and Y edges, and the current length of the diagonal edge, a computer system 160 may compute either the corresponding strain tensor or the corresponding affine transformations or deformation gradient. Further details of these calculations are provided below.

The computer system 160 may be a local computer system coupled to the data collector. In another embodiment, the computer system 160 may be a remote computer system, server, or distributed or cloud computing environment. The computer system 160 in one embodiment includes an input system to receive data about the lengths of the X and Y edges, data from force transducers, and other data, a processor to utilize the data to make calculations, and an output mechanism to control the drive controllers 190, and provide the data to the user. In one embodiment, the computer system 160 may include a plurality of different systems. That is, there may be a computer local to the material testing system to collect data and/or control the drive controllers, a wired or wireless connection to send the data collected to a remote system for processing, and a server or other host system to make the results of the processing available to users and/or further applications.

In one embodiment, the fabric is attached to the tracks using pins. The pins used to attach the cloth to the tracks each contain a 2D force transducer. The force transducer measures the X-Y components of force exerted by the cloth sample on the pin. These force data are used to determine the stress in the cloth sample. In one embodiment, for other materials, the pins may be replaced by another type of attachment mechanism appropriate for the material being tested.

In one embodiment, each of the attachment hardware force transducers are coupled to a sensor data collector 155. The sensor data collector receives data from all of mounts, the free mounts and the corner mounts as well. In one embodiment, there may be wire connections 150 between each of the mounts and the sensor data collector 155. In another embodiment, the connection may be a wireless connection.

The sensor data collector 155 sends the data to computer system 160. The drive controller 190 also sends the data to the computer system 160. The computer system 160 utilizes the data to calculate the effect of the various types of force on the fabric. This data is stored in memory 180, in one embodiment in a database, which is used for characterizing fabrics in simulation. The memory 180 may be a remote database system.

In one embodiment, the linear actuators in the drives 115A, 115B, 115C are adjusted by drive controller 190 to systematically explore combinations of stretch and shear. To minimize the effects of hysteresis, in one embodiment the exploration orders the configurations with the least amount of strain to be tested before configurations with greater strain. In one embodiment, the system tests multiple samples of a given fabric to reduce measurement variance. When this is done, the ordering of strain states for testing may also be varied to further help minimize hysteresis effects.

In one embodiment, the system in addition to receiving force data also can take pictures of the fabric under various types of strain. In one embodiment, a trigger 170 may trigger one or more cameras 175 to take one or more photographs, sequences of photographs and/or videos. In one embodiment, the camera(s) may be fixed above the base and frame at a fixed location. In another embodiment, the camera(s) may be moveable, so that it can obtain images from multiple angles, and/or there may be multiple cameras. In one embodiment, the trigger 170 may also control lights 178. This feature enables the camera 175 to take images under various lighting conditions. This data can be useful in characterizing the appearance of a fabric in simulation and in determining whether the fabric appearance changes at various states of strain.

Figure 1B:
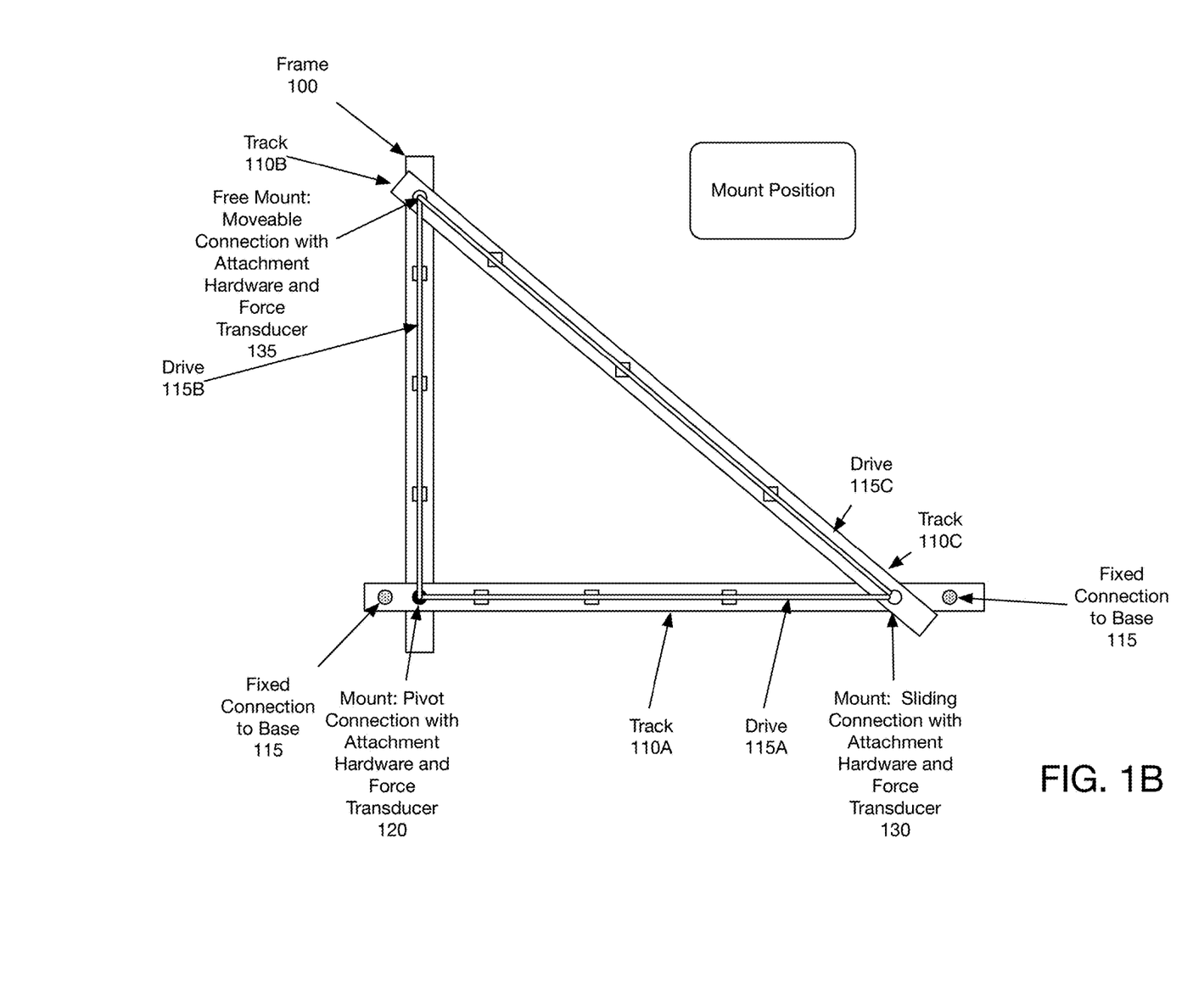
FIG. 1B is an overview diagram of one embodiment of the track drive and measurement system.

FIG. 1B illustrates one embodiment of the system to monitor the configuration of the tracks. The relative position of each of the tracks 110A, 110B, 110C define the strain applied to the fabric 145 in all directions. In one embodiment, an extension tracker 199 determines the extension of each of the tracks 110A, 110B, 110C. In one embodiment, a track 110A is adjusted using track drive 192A. In one embodiment, track drive 192A is a screw-based drive which permits adjustment of the positions of the mounts at the corner of fabric 145. This adjusts the direction(s) and strength of the strain. The track drive 192A, 192B, 192C may be adjusted by other mechanisms, in one embodiment.

The configuration of each track 110A, 110B, 110C is tracked by extension tracker 199. Extension tracker 199 may have one or more of a plurality of methods of determining the precise length between the corner mounts of each track. Extension tracker 199 may be an optical reader 194A, 194B, 194C, a mechanical sensor 198A, 198B, 198C, or a camera 196. In one embodiment, the camera 196 may be separate cameras for each of the tracks. In another embodiment, the camera 196 may include separate image sensors (cameras) for each of the tracks 110A, 110B, 110C. This extension tracker 199 determines how far extended each of the tracks 110A, 110B, 110C are. The extension tracker 199 provides data used to determine the frame configuration. The frame configuration data is used in evaluating the strain on the fabric 145, for various settings.

Figure 2:
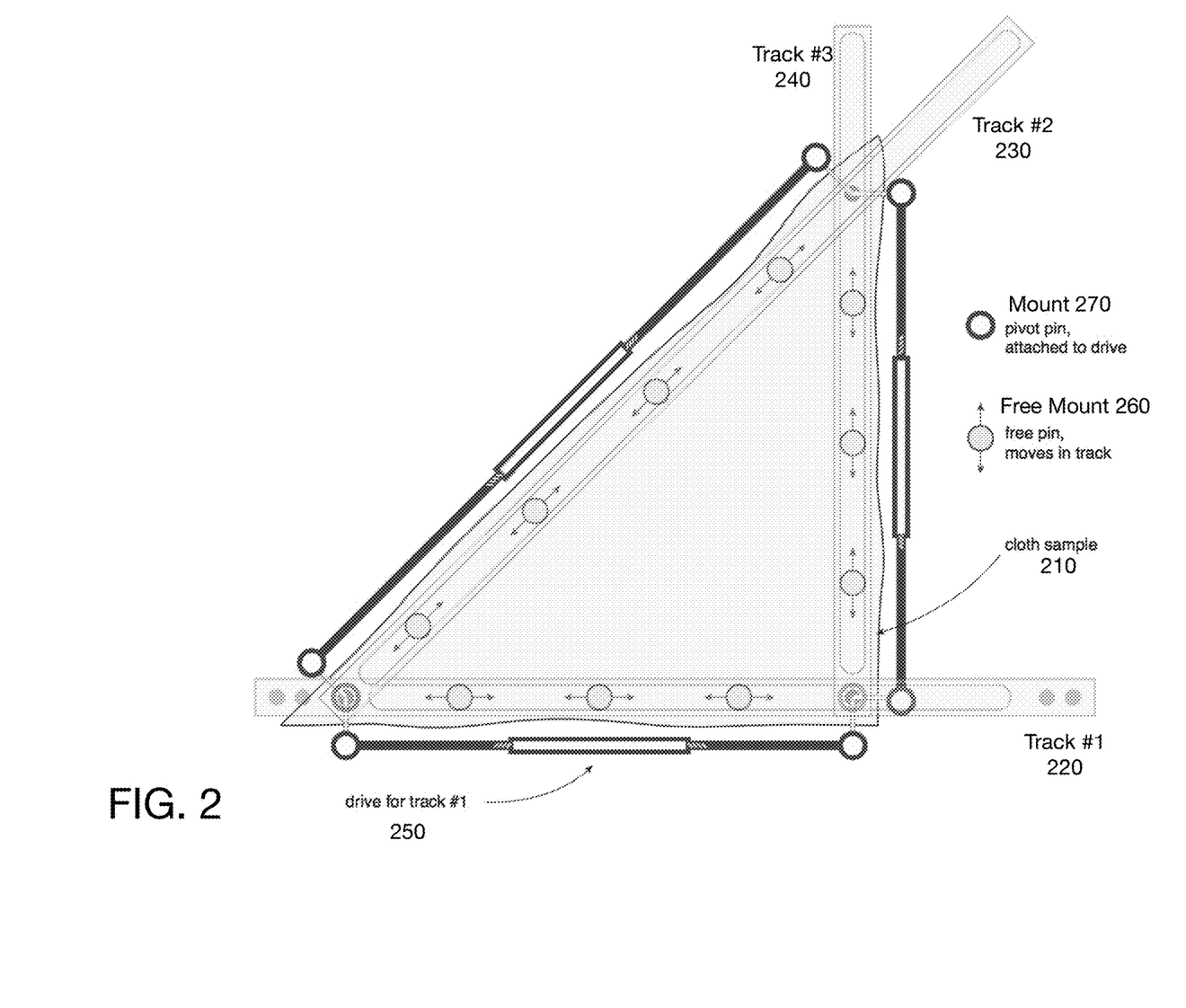
FIG. 2 is a simplified diagram of the track layout of one embodiment of the system.

FIG. 2 is a simplified diagram of the track layout of one embodiment of the system. The fabric 210 is coupled to the tracks 220, 230, 240 via mounts, including mounts 270 which are pivot pins and free mounts 260. The positioning of the tracks is defined by drives 250, which are attached to the pivot pins. In one embodiment, as shown, the drives 250 may simply be metal rods which can be changed in length via a screw drive or similar actuator. In another embodiment, the drives 250 may be implemented electronically or may be implemented using other methods.

The process starts when the cloth sample 210 is coupled to the frame. This is done by attaching the cloth sample to each of the mounts 270 in the corners of the frame. In one embodiment, this is done with a relaxed fabric configuration so that the fabric is not under strain.

The free mounts 260 are then attached to the fabric. In one embodiment, the free mounts 260 are attached at regular intervals, for example every 3 inches. For testing, the drives 250 are adjusted, to apply the testing stretch and/or shear to the fabric. In one embodiment, a sequence of different testing configurations is utilized, and the system records the strain for each of the different testing configurations. In one embodiment, this is used to build up a table of results, which is used to characterize the mechanical properties of the fabric. This data is used in fabric simulation, in one embodiment.

Figure 4:
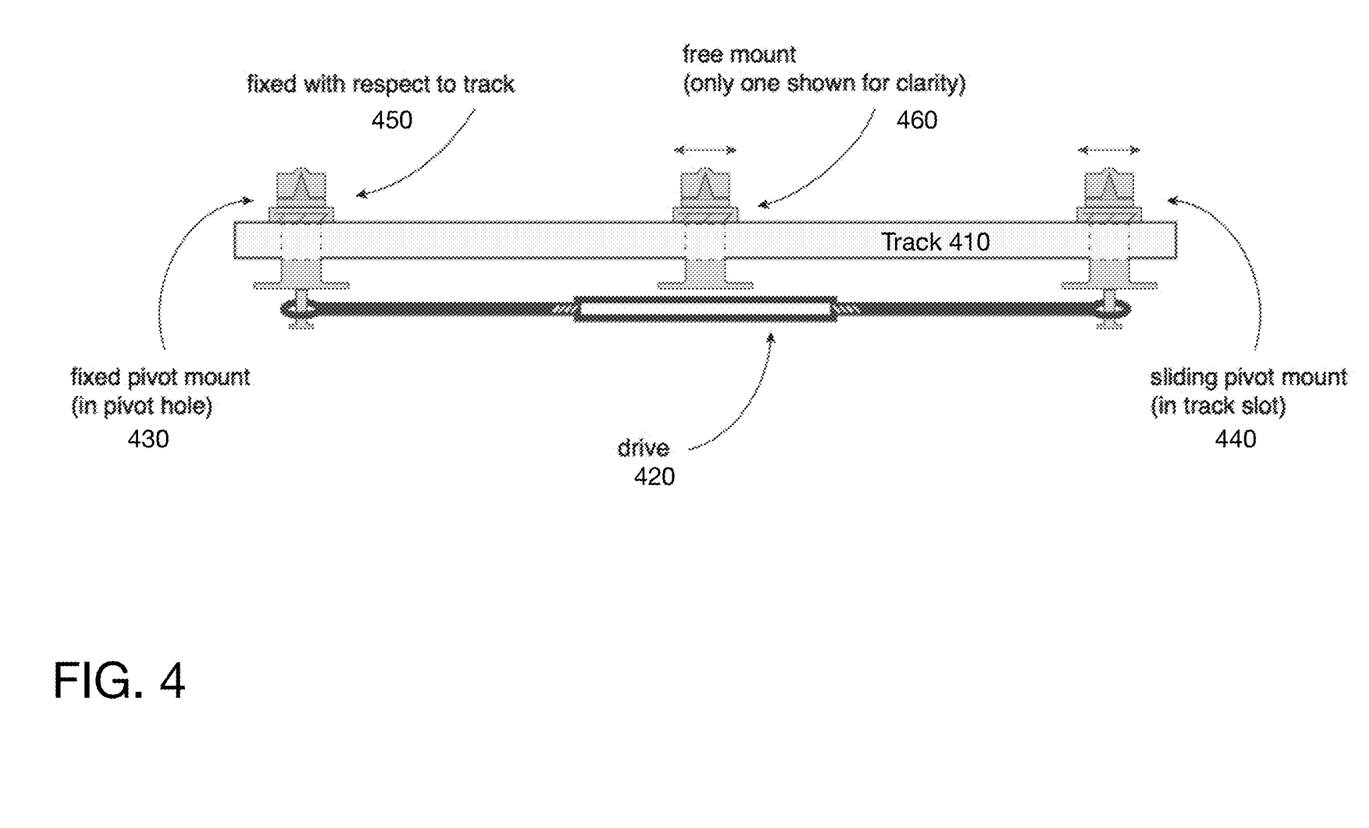
FIG. 4 is an illustration of one embodiment of a track and a drive including a pivot mount pin.

FIG. 4 is an illustration of one embodiment of a track and a drive including a pivot mount pin. The single track 410 may be any of the three tracks (or more tracks in other configurations). The track 410 includes in this illustration three types of mounts: a fixed mount 440, a pivotably movable mounts 440, and free mount 460 which slides in the track slot (not shown). In this example, the drive 420 is attached to the two end mounts, to enable adjusting the size of the triangle (or shape) made by the frame. In one embodiment, the drive may be coupled using a simple loop coupled to the base of the mount. As the screw is adjusted in the drive 420, the distance between the mounts 450, 440 increases or decreases. In one embodiment, the precise position of the drive is recorded as a parameter. In one embodiment, rather than manual adjustment of a screw, the screw may be automatically adjusted using an actuator. The actuator may be electric, pneumatic, mechanical, or another type of actuator.

The free mount moves freely within the slot in the track 410. This allows the free mount, which is coupled to the cloth, to move to a position of least resistance. In one embodiment, the slot is kept sufficiently smooth that the movement of the mount can be considered to be frictionless. The transducers in the mounts measure the force being exerted on the cloth, and its effect.

Figure 5:
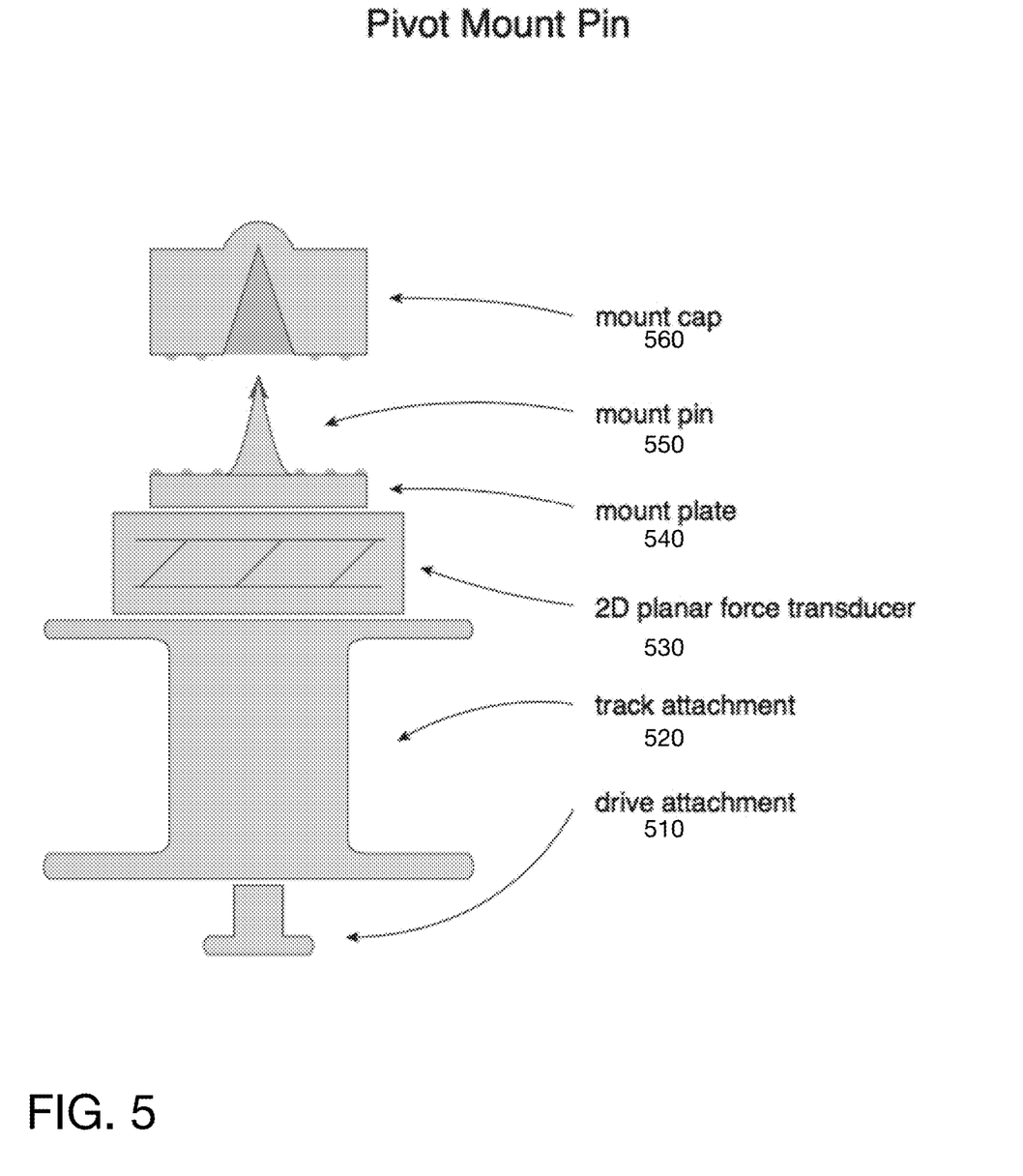
FIG. 5 is an illustration of one embodiment of a pivot mount pin.

FIG. 5 is an illustration of one embodiment of a mount pin. This is one embodiment of the pins to which a drive is attached, e.g. pin 430 or 440 in FIG. 4. The drive attachment 510 is the portion of the mount that extends below the slot in the track, and to which the drive is coupled. In one embodiment, it's a simple screw-in element, to which a loop in the drive is coupled.

The track attachment 520 is the portion of the mount pin which slides within the slot in the track. In one embodiment, the mounts are customized to fit within the slot in the track with no significant side-to-side movement in any direction. In one embodiment, the slot is sized such that the mount pins have movement only along a single axis (e.g. along the slot).

The force transducer 530 measures the force exerted on the mount plate 540 by the cloth, which is attached to the mount via pin 550 and fixed in place by mount cap 560. Though the mount pin 550 is illustrated as a pin which is useful for thinner fabrics, one of skill in the art would understand that the configuration of the mount pin 550 may be adjusted based on fabric type. In one embodiment, for some fabrics a clip may be used, instead of a pin. For some fabrics a thin sharp pin may be used. For some fabrics, a flatter pin shape may be used. The purpose of the mount pin 550 and cap 560 is to fix the fabric to the frame in a way that the fabric cannot move, since such movement would result in incorrect characterization data.

Figure 6:
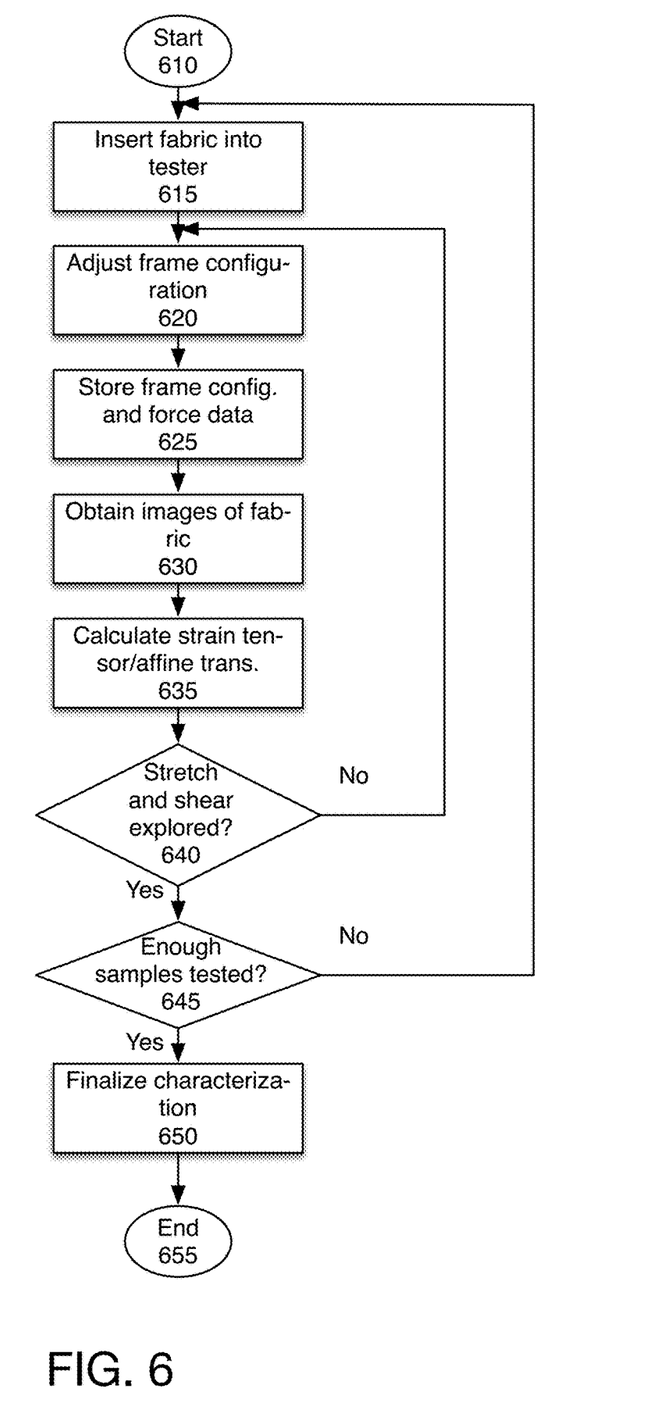
FIG. 6 is a flowchart of one embodiment of testing a planar material.

FIG. 6 is a flowchart of one embodiment of testing fabric. The process starts at block 610.

At block 615, the fabric is inserted in the tester. In one embodiment for a triangle shaped frame, the initial configuration of the frame is established by adjusting the linear actuators so that the frame forms a right triangle of approximately the same dimensions as the piece of fabric.

At block 620, the configuration of the frame is adjusted, adding a stretching and/or shear to the fabric.

At block 625, the system stores the frame configuration data and the measured force on each of the mount pins, for this configuration.

At block 630, in one embodiment, one or more images of the fabric are taken. In one embodiment, these image may be taken under different lighting conditions, and/or from different angles.

At block 635, the system calculates the strain tensor or affine transformation for the fabric at a given configuration. Given the initial lengths of the X and Y edges, the current lengths of the X and Y edges, and the current length of the diagonal edge, one may compute either the corresponding strain tensor or the corresponding affine transformation.

At block 640, the process determines whether the stretch and shear have been explored for this fabric. If not, the process returns to block 620 to adjust the fabric to another configuration. The system systematically explores combinations of stretch and shear.

If the stretch and shear have been explored, the process continues to block 645.

At block 645, the process determines whether a sufficient number of samples have been tested for this fabric. In one embodiment, to ensure accuracy a first set of samples are tested. In one embodiment, at least three samples of a fabric are tested. In one embodiment, after testing the first set of samples, the system determines whether the results from the tested samples have produced consistent results. If not, the system requires further testing. In one embodiment, the process tests the fabric until a preset number of samples have produced consistent results. In one embodiment, if multiple samples produce disparate results, the system alerts the user. This may be the result of incorrect mounting of the fabric, having samples from different batches that have significantly different characteristics, system error, or another issue.

If the process determines that the number of samples is not sufficient, the system returns to block 615, and the system prompts the insertion of another piece of the fabric into the tester.

If a sufficient number of samples have been tested, the process continues to block 650. At block 650 the system builds up a mechanical parameter characterization of the fabric. This characterization data may then be used in simulations and other uses. The data may also be made available to companies interested in using a particular fabric, for example. The process then ends at block 655.

A strain tensor may be used in one embodiment to quantify how much a sample of material has been stretched/compressed and/or sheared. A strain tensor provides a way of quantifying the elastic forces that are attempting to restore a stretched, compressed, and/or sheared sample back to its original shape. The functional relationship that allows computing stress given strain is referred to as a constitutive model. The constitutive model may be inferred from analyzing multiple pairs of strain and stress measurements. Computer simulations of fabric and other materials in one embodiment use a constitutive model.

For the case of a planar sample of material, the strain may be represented either in matrix form:

$$E_m = \begin{bmatrix} E_{xx} & E_{xy} \\ E_{yx} & E_{yy} \end{bmatrix}$$

Or in vector form:

$$E_v = \begin{bmatrix} E_{xx} \\ E_{yy} \\ E_{xy} \end{bmatrix}$$

The quantities Exx, Eyy, and Exy respectively relate to the stretch/compression in the X and Y directions and the shear. Due to symmetry the Exy and Eyx quantities are constrained to be the same.

Different mathematical formulations exist for computing a strain tensor. In one embodiment, the Green-Lagrange formulation is used. A person skilled in the art will recognize that other strain formulations may be used in place of the Green-Lagrange formulation.

The Green-Lagrange formulation for Exx, Eyy, and Exy is given by:

$$E_{xx} = \left(\frac{\partial d}{\partial x} \cdot \frac{\partial d}{\partial x} - 1\right)/2$$

$$E_{yy} = \left(\frac{\partial d}{\partial y} \cdot \frac{\partial d}{\partial y} - 1\right)/2$$

$$E_{xy} = \left(\frac{\partial d}{\partial x} \cdot \frac{\partial d}{\partial y}\right)/2$$

Where d is the deformation function that relates the original shape of a sample to the deformed (combination or stretch, compression, and shear) configuration that the strain is measuring. If F is the gradient of the deformation function, then the Green-Lagrange formulation may equivalently be written as:

$$E_m = \frac{1}{2}(F^T \cdot F - I)$$

A person skilled in the art will recognize that F may also be referred to as an affine transformation. The centered dot represents matrix multiplication.

Referring to FIG. 2, let A1, B1, and C1 respectively denote the positions in the XY plane of mount points 120, 130, 135 when the material sample is initially mounted in the testing device, and let A2, B2, and C2 respectively denote the positions in the XY plane of mount points 120, 130, 135 when the material sample has been deformed to some test configuration. The deformation gradient F corresponding to the test configuration may be computed as:

$$F = [(B_2 - A_2)(C_2 - A_2)] \cdot [(B_1 - A_1)(C_1 - A_1)]^{-1}$$

In the above equation, A1, B1, C1, A2, B2, and C2 are column vectors in R2 and the square brackets indicate formation of a 2×2 matrix using the vectors as columns.

Thus, the testing device can be configured to deform the material sample by adjusting the tracks. For each such configuration a corresponding strain tensor may be computed given the positions of the mount points. In one embodiment the mount point positions are determined from the extension tracker's measuring the position of the track drives. In one embodiment, an optical reader, mechanical sensor, a camera, or similar device may be used to observe the positions of the mount points.

In the case of an embodiment that determines the mount-point locations, A, B, and C, from the track lengths, geometric equations may be used to compute A, B, and C. If L1, L2, and L3 are the respectively the measured distances between A-B, B-C, and C-A then the following equations compute the locations of A, B, and C:

$$A = \begin{bmatrix} 0 \\ 0 \end{bmatrix}$$

$$B = \begin{bmatrix} L_1 \\ 0 \end{bmatrix}$$

$$C = \begin{bmatrix} C_x \\ C_y \end{bmatrix}$$

$$C_x = \frac{l_1^2 - l_2^2 + l_3^2}{2l_1}$$

$$C_y = \frac{\sqrt{-(l_1 - l_2 - l_3)(l_1 + l_2 - l_3)(l_1 - l_2 + l_3)(l_1 + l_2 + l_3)}}{2l_1}$$

A person skilled in the art will recognize that the other equations could be used to compute the locations, A, B, and C when given the lengths L1, L2, and L3. Furthermore, a person skilled in the art will recognize than an XY coordinate system with A at the origin and B along the X axis is used here for convenience and simplicity of expression, but other coordinate systems could be used with a corresponding transformation of the equations to produce equivalent results.

The force transducers measure the resulting forces generated by the material sample in each test configuration. The constitutive model relates strain to stress, so the combination of the strain measurement and force measurement for a plurality of different configurations allows a constitutive model to be determined by fitting the parameters of the constitutive model to the observed data. In one embodiment a non-linear constitutive model, such as the WRO model described by Huamin Wang et al. in "*Data-Driven Elastic Models for Cloth: Modeling and Measurement*" may be used. Other constitutive models may also be used.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A material testing apparatus comprising:
a frame having three or more tracks;
a plurality of mounts positioned within the three or more tracks, the mounts including an attachment mechanism to attach the mounts to a material being tested, a subset of the mounts including a force measurement element, the plurality of mounts including a subset of free mounts that move freely in a track slot within the track to any position within the track; and
a data collector to collect data from the force measurement elements in the subset of mounts when the material is placed under stress, to characterize the material.

2. The material testing apparatus of claim 1, wherein the frame comprises three tracks arranged in a triangle form.

3. The material testing apparatus of claim 2, wherein the frame comprises:
a first track fixed to a base, the first track including a first track slot;
a second track pivotally coupled to the first track, and having a second track slot;
a third track movably coupled to the first track slot in the first track, and movably coupled to the second track slot in the second track.

4. The material testing apparatus of claim 3, wherein each of the tracks are coupled using mounts, such that the material tested is a triangular shape and is coupled to the mounts at three corners.

5. The material testing apparatus of claim 1, wherein the force measurement element comprises a force transducer and further comprising:
the data collector coupled to each of the mounts via a wired connection;
a computer system to calculate characteristics of the cloth under stretch and/or shear; and
a database of material characteristics.

6. The material testing apparatus of claim 5, wherein the computer system associates parameters of each test with the characteristics of the material, the parameters including a configuration of the frame and force measurement data from the plurality of mounts.

7. The material testing apparatus of claim 1, further comprising:
a camera to obtain images of the material during testing.

8. The material testing apparatus of claim 7, further comprising:
one or more lights to provide a variety of lighting conditions, for the images;
wherein the camera obtains a plurality of images including one or more of: a plurality of angles, a plurality of heights, a plurality of lighting conditions.

9. A method of testing a material comprising:
providing a frame including a plurality tracks and a plurality of mount pins including free mounts, at least a subset of the mount pins including a force transducer;
adjusting a configuration of the frame, after the material is inserted into the frame, by attachment to the mount pins;
storing configuration data and force data obtained for the configuration;
calculating a strain tensor or affine transformation, based on the configuration data and the force data.

10. The method of claim 9, further comprising:
adjusting the configuration of the frame, to obtain data for a plurality of configurations.

11. The method of claim 9, further comprising:
storing a characterization of the material based on the calculated strain tensor or affine transformation.

12. The method of claim 9, wherein the frame comprises three tracks arranged in a triangle form.

13. The method of claim 12, wherein the frame comprises a first track fixed to a base, the first track including a first track slot, a second track pivotally coupled to the first track, and having a second track slot, and a third track movably coupled to the first track slot in the first track, and movably coupled to the second track slot in the second track.

14. The method of claim 13, wherein each of the tracks are coupled using mounts, such that a triangular material being tested is coupled to the mounts at its three corners.

15. The method of claim 9, comprising:
coupling a data collector to each of the mounts via a wired connection;
calculating characteristics of the material under stretch and/or shear by a computer system; and populating a database of material characteristics, based on the characteristics, the configuration data, and the force data.

16. The method of claim 15, further comprising:
associating parameters of each test with the characteristics of the material, the parameters including a configuration of the frame and force measurement data from the plurality of mounts.

17. The method of claim 9, further comprising:
obtaining a plurality of images of the material during testing.

18. The method of claim 17, further comprising:
altering one or more lights to provide a variety of lighting conditions, for the images.

19. The method of claim 18, wherein the camera obtains a plurality of images including one or more of images from: a plurality of angles, a plurality of heights, and a plurality of lighting conditions.

20. A material testing apparatus comprising:
a frame having three tracks arranged in a triangle form, the three tracks moveably coupled to each other;
a plurality of mounts positioned within the tracks, the mounts including an attachment mechanism to attach the mounts to a material being tested, the mounts including a force measurement element, one or more free mounts that move freely in a track slot within the track to any position within the track; and
a data collector to collect data from the force measurement elements in the subset of mounts when the material is placed under stress, to characterize the material; and
a computer system to calculate characteristics of the cloth under stretch and/or shear and build a database of material characteristics.

\* \* \* \* \*